(12) United States Patent
Burt (10) Patent No.: US 10,813,955 B2
(45) Date of Patent: Oct. 27, 2020

(54) METHODS FOR TREATING AGE-RELATED ORGAN OR TISSUE DYSFUNCTION THROUGH HETEROCHRONIC TRANSBIOSIS USING NONVIABLE PLURIPOTENT STEM CELLS

(71) Applicant: Richard K. Burt, Chicago, IL (US)

(72) Inventor: Richard K. Burt, Chicago, IL (US)

(73) Assignee: Genani Corporation, Chicago, IL (US)

( * ) Notice: Subject to any disclaimer, the term of this patent is extended or adjusted under 35 U.S.C. 154(b) by 59 days.

(21) Appl. No.: 15/276,120

(22) Filed: Sep. 26, 2016

(65) Prior Publication Data

US 2017/0106024 A1    Apr. 20, 2017

Related U.S. Application Data

(60) Provisional application No. 62/234,444, filed on Sep. 29, 2015.

(51) Int. Cl.

| A61K 35/545 | (2015.01) |
| A61K 9/08 | (2006.01) |
| A61K 9/00 | (2006.01) |
| A61K 47/26 | (2006.01) |
| A61K 9/19 | (2006.01) |

(52) U.S. Cl.
CPC ............ *A61K 35/545* (2013.01); *A61K 9/08* (2013.01); *A61K 9/0019* (2013.01); *A61K 9/19* (2013.01); *A61K 47/26* (2013.01)

(58) Field of Classification Search
CPC ........ A61K 35/545; A61K 9/08; A61K 47/26; A61K 9/0019; A61K 9/19; A61P 25/00
See application file for complete search history.

(56) References Cited

U.S. PATENT DOCUMENTS

| 5,486,359 A | 1/1996 | Caplan | |
| 5,827,735 A | 10/1998 | Young | |
| 5,837,539 A | 11/1998 | Caplan | |
| 7,311,905 B2 | 12/2007 | Hariri | |
| 8,187,881 B2 | 5/2012 | Smith | |
| 9,017,658 B2 | 4/2015 | Burt | |
| 9,364,425 B2 | 6/2016 | Burt | |
| 9,381,151 B2 | 7/2016 | Burt | |
| 9,757,422 B2 | 9/2017 | Burt | |
| 9,867,855 B2 | 1/2018 | Burt | |
| 2002/0188963 A1 | 12/2002 | Loring | |
| 2004/0151704 A1 | 8/2004 | Berenson | |
| 2004/0180043 A1* | 9/2004 | Sabbah | C12N 5/0663 424/93.21 |
| 2005/0106724 A1 | 5/2005 | Schierholz | |
| 2005/0255588 A1 | 11/2005 | Young | |
| 2006/0233766 A1 | 10/2006 | Messina | |
| 2007/0092494 A1 | 4/2007 | Higgins | |
| 2007/0274960 A1 | 11/2007 | Harman | |
| 2007/0292401 A1 | 12/2007 | Harmon | |
| 2008/0241113 A1 | 10/2008 | Walton | |
| 2009/0214491 A1* | 8/2009 | Burt | A61K 41/00 424/93.7 |
| 2010/0209398 A1 | 8/2010 | Tankovich | |
| 2011/0020291 A1 | 1/2011 | Banerjee | |
| 2011/0212062 A1 | 9/2011 | Falanga | |
| 2012/0141433 A1 | 6/2012 | Tankovich | |
| 2013/0243739 A1* | 9/2013 | Burt | A61K 8/982 424/93.7 |
| 2014/0255357 A1* | 9/2014 | Burt | A61K 8/982 424/93.7 |
| 2016/0022744 A1 | 1/2016 | Burt | |
| 2018/0133371 A1 | 5/2018 | Peterson | |
| 2018/0161379 A1 | 6/2018 | Peterson | |

FOREIGN PATENT DOCUMENTS

| CN | 101156944 | 4/2008 | |
| CN | 101449822 | 6/2009 | |
| CN | 103751228 | 4/2014 | |
| WO | 2004007697 | 1/2004 | |
| WO | 2006071802 | 7/2006 | |
| WO | 2008011524 | 1/2008 | |
| WO | WO-2013142192 A1 * | 9/2013 | ............ A61K 8/982 |

OTHER PUBLICATIONS

Rosello et al. "Mammalian genes induce partially reprogrammed pluripotent stem cells in non-mammalian vertebrate and invertebrate species" eLife. 2013; 2: e00036. (Year: 2013).*
Johnson, Andrew. "Mexican salamander helps uncover mysteries of stem cells and evolution." UK National Stem Cell Network 2010 retrieved conference. online from https://www.eurekalert.org/pub_releases/2010-07/babs-msh070910.php. (Year: 2010).*
Rubio et al. "Cell-Based Fish: A Novel Approach to Seafood Production and an Opportunity for Cellular Agriculture" Front. Sustain. Food Syst., Jun. 11, 2019 (Year: 2019).*
Li et al. "An Insight on Small Molecule Induced Foot-Print Free Naive Pluripotent Stem Cells in Livestock." (2015) Stem Cell Discovery 05(01):1-9 (Year: 2015).*
Anderson et al. "Achieving stable human stem cell engraftment and survival in the CNS: is the future of regenerative medicine immunodeficient?" Regen Med. May 2011; 6(3): 367-406. (Year: 2011).*
Chiavegato et al. "Human amniotic fluid-derived stem cells are rejected after transplantation in the myocardium of normal, ischemic, immuno-suppressed or immuno-deficient rat" Mol Cell Cardiol. Apr. 2007;42(4):746-59 (Year: 2007).*

(Continued)

*Primary Examiner* — Titilayo Moloye
(74) *Attorney, Agent, or Firm* — Fitch Even Tabin & Flannery LLP (57) ABSTRACT

The disclosure is directed to the use of nonviable pluripotent stem cells to improve age-related declines in tissue and organ function. In one aspect, nonviable pluripotent stem cells are used to improve cognition in a subject in need thereof. In another aspect, nonviable pluripotent stem cells are used to improve age-related cardiac dysfunction in a subject in need thereof. Administration of nonviable pluripotent stem cells provides a transient and safe form of heterochronic cellular transbiosis.

6 Claims, 4 Drawing Sheets

(56) References Cited

OTHER PUBLICATIONS

Lalit et al. "Induced Pluripotent Stem Cells for Post-Myocardial Infarction Repair" Circ Res. Apr. 11, 2014;114(8):1328-45. (Year: 2014).*

Thum et al. "The dying stem cell hypothesis: immune modulation as a novel mechanism for progenitor cell therapy in cardiac muscle." J Am Coll Cardiol. Nov. 15, 2005;46(10):1799-802. (Year: 2005).*

Baht, Gurpreet S., et al. "Exposure to a Youthful Circulation Rejuvenates Bone Repair Through Modulation of Beta-Catenin." Nature Communications, published May 19, 2015, 9 pages.

Brown, Kristy J., et al., "Advances in the Proteomic Investigation of the Cell Secretome." Expert Rev Proteomics, Jun. 2012, vol. 9, No. 3, pp. 337-345.

Burt, Richard K., et al., "Mitotically Inactivated Embryonic Stem Cells Can Be Used as an In Vivo Feeder Layer to Nurse Damaged Myocardium after Acute Myocardial Infarction." Circulation Research, Oct. 26, 2012, vol. 111, pp. 1286-1296.

Choi, Dong-Sic, et al., "Proteomics of Extracellular Vesicles: Exosomes and Ectosomes." Mass Spectrometry Reviews, 2015, vol. 34 pp. 474-490.

Chute, John P., et al., "Ex vivo culture rescues hematopoietic stem cells with long-term repopulating capacity following harvest from lethally irradiated mice." Experimental Hematology, vol. 32, 2004, pp. 308-317.

Conboy, Irina M., et al., "Rejuvenation of Aged Progenitor Cells by Exposure to a Young Systemic Environment." Nature, vol. 433, Feb. 17, 2005, pp. 760-764.

Conboy, Michael J. et al., "Heterochronic Parabiosis: Historical Perspective and Methodological Considerations for Studies of Aging and Longevity." Aging Cell, Jun. 2013, vol. 12, pp. 525-530.

Dai, Wangde, et al., "Myocardial Regeneration by Embryonic Stem Cell Transplantation: Present and Future Trends." Expert Review of Cardiovascular Therapy, vol. 4, No. 3, May 2006, pp. 375-383.

Eggel, Alexander, et al., "A Revival of Parabiosis in Biomedical Research." The European Journal of Medical Sciences: Swiss Medical Weekly, Feb. 4, 2014, vol. 144, 9 pages.

Eichwald, E. J., et al., "The Anemia of Parabiotic Intoxication." Annals of the New York Academy of Sciences, vol. 87, Dec. 2006, pp. 119-132.

Fraidenraich, Diego, et al., "Rescue of Cardiac Defects in Id Knockout Embryos by Injection of Embryonic Stem Cells." Science, Oct. 8, 2004, vol. 306, pp. 247-252.

Hassink, Rutger J., et al., "Stem Cell Therapy for Ischemic Heart Disease." Trends in Molecular Medicine, Oct. 2003, vol. 9, pp. 436-441.

Heng, B.C., et al., "Utilizing Human Embryonic Stem Cells as 'Catalysts' for Biological Repair and Regeneration: Challenges and Possible Strategies." Clinical and Experimental Medicine, May 2005, vol. 5, No. 1, pp. 37-39.

Heng, Boon Chin, et al., "Potential Benefits of Co-transplanting Autologous Adult Stem Cells Together With Human Embryonic Stem Cells or Their Differentiated Derivatives." Annals of Clincal and Laboratory Science, vol. 35, No. 1, Jan. 2005, pp. 3-6.

Heng, Boon Chin, et al., "Transplanted Human Embryonic Stem Cells as Biological 'Catalysts' for Tissue Repair and Regeneration." Medical Hypotheses, vol. 64, No. 6, 2005 pp. 1085-1088.

Higashiyama, Takanobu. "Novel Functions and Applications of Trehalose*" Pure Appl. Chem, 2002, vol. 74, No. 7, pp. 1263-1269.

Hodgson, Denice M., et al., "Stable Benefit of Embryonic Stem Cell Therapy in Myocardial Infarction." Am. J. Physiol. Heart Circ. Physiol., 2004, 287 (2), H471-H479.

Ke, Qingen, et al., "Embryonic Stem Cells Cultured in Biodegradable Scaffold Repair Infarcted Myocardium in Mice." Acta Physiologica Sinica, 2005, 57 (6), pp. 673-681.

Lee, Jong-Kuen, et al., "Exosomes Derived from Mesenchymal Stem Cells Suppress Angiogenesis by Down-Regulating VEGF Expression in Breast Cancer Cells." PLOS ONE, Dec. 2013, vol. 8, issue 12, pp. 1-11.

Loffredo, Francesco S., et al., "Growth Differentiation Factor 11 Is a Circulating Factor that Reverses Age-Related Cardiac Hypertrophy." Cell, May 9, 2013, vol. 153, No. 4, pp. 828-839.

Ruckh, Julia M., et al., "Rejuvenation of Regeneration in the Aging Central Nervous System." Cell Stem Cell, Jan. 6, 2012, vol. 10, pp. 96-103.

Schey, Kevin L., et al., "Proteomics Characterization of Exosome Cargo." Methods, Mar. 2015, <http://doi.org/10.1016/j.ymeth.2015.03.018>, pp. 1-8.

Song, Guodong, et al., "Use of Parabiotic Model in Studies of Cutaneous Wound Healing to Define Participation of Circulating Cells." Wound Repair Regeneration, 2010, vol. 18, No. 4, pp. 426-432.

Tauro, Bow J., et al., "Two Distinct Populations of Exosomes Are Released from LIM1863 Colon Carcinoma Cell-Derived Organoids." Molecular & Cellular Proteomics, 12.3, 2013, pp. 587-597.

Trounson, Alan. "Human Embryonic Stem Cells: Mother of All Cell and Tissue Types." Reproductive Biomedicine Online, Reproductive Healthcare Ltd, Cambridge, vol. 4, No. 1, Jan. 1, 2002, pp. 58-63.

Villeda, Saul A. et al., "Young Blood Reverses Age-Related Impairments in Cognitve Function and Synaptic Plasticity in Mice." 2014, Nature Medicine, vol. 20, pp. 659-663, 8 pages.

Watson, G.E., et al., "Long-term in Vivo Transmission of Alpha-particle-induced Chromosomal Instability in Murine Haemopoietic Cells." International Journal of Radiation Biology, vol. 69, No. 2, 1996, pp. 175-182.

Kortekaas, Rudie, et al., "Blood-Brain Barrier Dysfunction in Parkinsonian Midbrain In Vivo." Annuals of Neurology, 2005, vol. 57, pp. 176-179.

Schiffer, Wynne K. et al., "Optimizing Experimental Protocols for Quantitative Behavioral Imaging with F-FDG in Rodents." Journal of Nuclear Medicine, 2007, vol. 48, pp. 277-287.

Singapore Patent Application No. 10201608144U, Written Opinion, dated Sep. 19, 2019, 7 pages.

Singapore Patent Application No. 10201608144U, Search Report, dated Jul. 15, 2019, 4 pages.

Haider, Thomas, et al., "The Secretome of Apoptotic Human Perpheral Blood Mononuclear Cells Attenuates Secondary Damage Following Spinal Cord Injury in Rats." Experimental Neurology, May 2015, vol. 267, pp. 230-242.

Nation, Daniel A., et al., "Blood-Brain Barrier Breakdown Is an Early Biomarker of Human Cognitive Dysfunction." Nature Medicine, Feb. 2019, vol. 25, No. 2, pp. 270-276.

* cited by examiner

METHODS FOR TREATING AGE-RELATED ORGAN OR TISSUE DYSFUNCTION THROUGH HETEROCHRONIC TRANSBIOSIS USING NONVIABLE PLURIPOTENT STEM CELLS

CROSS REFERENCE TO RELATED APPLICATION

This application claims the benefit of U.S. Provisional Application No. 62/234,444, filed Sep. 29, 2015, which is hereby incorporated by reference in its entirety.

FIELD

This application relates to methods of treating age-related organ or tissue dysfunction, including age-related cognitive impairment.

BACKGROUND

Parabiosis is the surgical joining of two animals to create a shared circulation system. Heterochronic parabiosis is a well-documented phenomena whereby the vascular system of two animals of different ages are interconnected so that young blood cells transfer rejuvenating properties to the older animal. This allows the younger animal to reverse injury and age related degeneration in the older parabiont (1,2). In parabiotic pairings, the older conjoined parabiont improves, and the younger animal does not develop organ damage or accelerated aging (1,2). This indicates that the older parabiont is not secreting factors that cause aging but instead is deficient in factors that reverse aging, which are provided via the younger animal's circulatory system.

The mechanisms involved in heterochronic parabiosis remain incompletely understood. While multiple factors are involved, different cellular derived factor(s) have been attributed to play a partial role in reversal of aging of different organ systems. Following exposure of the aged animal to young blood, reversal of age related cardiac diastolic dysfunction (6), muscle satellite stem cell dysfunction (7), diminished osteoblast activation(8), and impaired neuro-synaptic plasticity (9) have been separately attributed at least in part to circulating cells from the younger parabiont providing Growth Differentiation Factor 11 (GDF-11) (6), enhanced expression activation of NOTCH ligand (7), B-catenin signaling (8), and activation of cyclic AMP response element binding protein (Creb) (9), respectively. In other cases, such as parabiont models of wound healing (10) and central nervous system remyelination (11), regeneration is ascribed directly to transfer of hematopoietic cells from the younger parabiont.

Despite these benefits, parabiont pairings, that is, the sharing of circulations between a younger and an older animal, is not practical due to ABO blood group incompatibilities. Parabiosis is also complicated by parabiotic intoxication, a form of runting disease or graft versus host disease (3), due to the immune cells of the younger animal attacking the organs of the older parabiont.

SUMMARY

The methods described herein are based on the discovery that nonviable pluripotent stem cells can be used to for transbiosis (heterochronic cellular transplantation) to improve age-related declines in tissue and organ function, including, for example, improving cognition, slowing the progression of age-related cognitive impairment, and improving age-related cardiac impairment.

As described herein, nonviable pluripotent stem cells are administered to a subject in need of treatment therewith to provide a physiologically younger phenotype and function to an organ or tissue by the transplantation of the nonviable pluripotent stem cells.

In one approach, a method is provided for improving cognition in a subject in need thereof, the method comprising administering a composition comprising an amount of nonviable pluripotent stem cells effective to improve cognition in the subject.

In another approach, a method is provided for slowing the progression of cognitive impairment in a subject with age-related cognitive impairment, the method comprising administering a composition comprising an amount of nonviable pluripotent stem cells effective to slow the progression of cognitive impairment in the subject.

In yet another approach, a method is provided for improving age-related organ or tissue dysfunction in a subject in need thereof, the method comprising administering a composition comprising an amount of nonviable pluripotent stem cells effective to improve age-related organ or tissue dysfunction in the subject.

The term "effective amount," "therapeutically effective amount," or similar phrase means the amount that will elicit the biological or medical response of a subject that is being sought by a medical doctor or other clinician. In one aspect, the term "effective amount" is intended to mean the amount that will bring about a biologically meaningful improvement in the treated subject. Successful treatment using the methods described herein can be determined by a skilled clinician based upon routine clinical practice.

The pluripotent stem cells useful herein are nonviable. Nonviable pluripotent stem cells, including pluripotent stem cells that have been lethally irradiated or lyophilized into a powder, remain capable of improving age-related declines in tissue and organ function, as well as repairing damaged organs or tissues in a subject. No adverse effects have been noted after treatment. At least in some approaches, it has been found that lyophilized pluripotent stem cells have better efficacy than lethally irradiated pluripotent stem cells.

The pluripotent stem cells useful herein can include pluripotent stem cells from all sources, such as but not limited to embryo, placenta, amniotic fluid, bone marrow, or those derived ex vivo from adult stem cells or adult somatic cells, and specifically includes embryonic stem cells (ESCs), modified adult stem or somatic cells (ASCs), that is, induced pluripotent stem cells (iPSC), and very small embryonic-like stem cells (VSELs).

DETAILED DESCRIPTION

Aging is believed to be a physiologic process at least in part due to the loss and or exhaustion of stem cells within the body. The methods described herein are based on the discovery that cells of a younger age or phenotype, particularly nonviable pluripotent stem cells, can be used to for transbiosis (heterochronic cellular transplantation) to improve age-related declines in tissue and organ function, including, for example, improving cognition, slowing the progression of age-related cognitive impairment, and improving age-related cardiac impairment. As described herein, nonviable pluripotent stem cells are administered to a subject in need of treatment therewith. In one aspect, the present methods are effective to provide a physiologically younger phenotype and function to an organ or tissue by the transplantation of the nonviable pluripotent stem cells. For example, the nonviable pluripotent stem cells may be administered to cardiac, nerve, muscle, bone, ocular, skin, liver, kidney, and lung tissues.

As used herein, "cognition" or "cognitive" or similar terms mean one or more mental abilities, including reasoning, judgment, perception, attention, memory, motor skills, language, coordination, intelligence, and visual and spatial processing. These mental abilities may decline at varying rates among individuals, and the age at which these abilities begin to decline may also vary among individuals.

In one approach, a method is provided for improving cognition in a subject in need thereof, the method comprising administering a composition comprising an amount of nonviable pluripotent stem cells effective to improve cognition in the subject. The method is effective to improve at least one of the above-mentioned mental abilities. In one particular approach, improving cognition specifically includes improving memory.

In another approach, a method is provided for slowing the progression of cognitive impairment in a subject with age-related cognitive impairment, the method comprising administering a composition comprising an amount of nonviable pluripotent stem cells effective to slow the progression of cognitive impairment of the subject. The method is effective to slow the progression of at least one of the above-mentioned mental abilities.

In yet another approach, a method is provided for improving age-related organ or tissue dysfunction in a subject in need thereof, the method comprising administering a composition comprising an amount of nonviable pluripotent stem cells effective to improve age-related organ or tissue dysfunction in the subject. For example, the age-related organ or tissue dysfunction may include, for example, cardiac dysfunction (e.g., reduced contractility (i.e., a reduction in the maximum change in pressure with respect to time (dp/dt) during systole) and diastolic relaxation (i.e., a reduction in the maximum change in pressure with respect to time (dp/dt) during diastole)).

Successful treatment using the methods described herein can be determined by a skilled clinician based upon routine clinical practice. For example, a number of screening tests for cognitive impairment are described in Cullen et al., "A review of screening tests for cognitive impairment," J. Neurol. Neurosurg. Psychiatry, 2007 August; 78(8): 790-99, which is incorporated herein by reference. Improved cardiac function can be determined by increased contractility and/or increased diastolic relaxation.

Advantageously, the improvement in age-related tissue and organ dysfunction described herein is not dependent on the permanent presence of the transplanted pluripotent stem cells in the target tissue or organ in the recipient. It is presently believed that the nonviable stem cells are cleared from the body within a short period of time. The recipient of the nonviable stem cells does not need immune suppression to allow lifelong engraftment because use of nonviable cells advantageously eliminates proliferation or growth when injected in vivo. Reducing or obviating the need for life long immunosuppression therapy can greatly improve a subject's comfort and quality of life. Advantageously, the nonviable cells do not form teratomas in vivo. Parabiosis-related graft versus host disease (runting disease) is also eliminated because there is no transfer of lymphocytes or other immune cells.

By "nonviable" is meant that the stem cells are prohibited from growing or dividing (i.e., growth arrested) and in fact are already dead (e.g., such as by lyophilization) or in the process of dying or undergoing apoptosis within a few days to weeks (e.g., such as by lethal irradiation). As used herein, nonviable cells may be produced by any method that causes growth arrest or cell death. In instances where the stem cells are made nonviable by lyophilization or similar technique, the lyophilization process kills the cells and the cells are not viable for any period of time after the lyophilization process or administration to the subject. The integrity of the cell membrane may or may not be maintained, but the cellular contents (such as the proteins, RNA, and lipids) of the cells should be preserved with minimal degradation such that function and activity of the contents are substantially maintained even though the cells are not viable.

In the methods described herein, the nonviable pluripotent stem cells are delivered in an effective amount to a subject in need of treatment. As used herein, the term "subject" includes mammals, such as but not limited to rodents, pigs, cats, dogs, and primates, and specifically includes humans. In at least some approaches, the subject is a human adult suffering from age related organ or tissue decline or dysfunction which may occur at any age. In at least some approaches, the subject may be generally healthy, at risk of developing a cognitive impairment, at risk of developing an age-related decline in tissue or organ function, have one or more symptoms of a cognitive impairment, or have one or more symptoms of an age-related decline in tissue or organ function. For example, a subject "at risk" of developing a cognitive impairment may have a family history of a cognitive impairment, carry a gene known or believed to be associated with a cognitive impairment, and/or have another medical condition associated with development of a cognitive impairment. Similarly, a subject "at risk" of developing an age-related decline in tissue or organ function may have a family history of a decline in tissue or organ function, carry a gene known or believed to be associated with a decline in tissue or organ function, and/or have another medical condition associated with development of a decline in tissue or organ function.

The term "effective amount" or "therapeutically effective amount" means the amount that will elicit the biological or medical response of a subject that is being sought by a medical doctor or other clinician. In one aspect, the term "effective amount" is intended to mean the amount that will bring about a biologically meaningful improvement in the treated subject. Data obtained from animal studies can be used in formulating a range of dosages for human use. The dosage may vary depending upon the dosage form employed, sensitivity of the patient, and the route of administration. The dosage suitable for a given subject can be determined by one of skill in the art. Generally, dosage and administration can be adjusted to provide or to maintain the desired effect.

Stem Cells

Pluripotent stem cells are capable of differentiating into more than one germ line or tissue specific lineage. Pluripotent stem cells have the potential to differentiate into endoderm, mesoderm, and ectoderm. As used herein, "pluripotent" can include pluripotent stem cells from all sources, such as but not limited to embryo, placenta, amniotic fluid, bone marrow, or those derived ex vivo from adult stem cells or adult somatic cells, and specifically includes embryonic stem cells (ESCs), modified adult stem or somatic cells (ASCs), that is, induced pluripotent stem cells (iPSC), and very small embryonic-like stem cells (VSELs). Pluripotent stem cells traditionally arise from the blastocyst stage of embryonic development and have the ability to develop into all types of fetal and adult cells except perhaps for placenta. Embryonic pluripotent stem cells (ESC) generally can be isolated from a 50- to 150-cell, 4- to 5-day-old post-fertilization blastocyst. While ESCs are capable of indefinite ex vivo proliferation, they exist only transiently in vivo during embryogenesis. Pluripotent stem cells have also been artificially generated (i.e., induced pluripotent stem cells (iPSC)) from other sources, such as placenta or from genetic manipulation of adult stem cells (ASC) or even adult somatic cells. ASC are located in tissues throughout the body and function as a reservoir to replace damaged or aging cells. ASC are generally restricted in their differentiation to cell lineages of the organ system from which they originate (i.e., "multipotent" stem cells), although recent research suggests that adult tissues, such as bone marrow, may harbor dormant pluripotent stem cells referred to as "very small embryonic-like stem cells" or "VSELs."

Supernumerary Human ESC lines may be obtained from in vitro fertilization clinic sources such as Human ESC line Cecol-14, obtained commercially from Cecolfes, Bogota, Colombia. Of course, other supernumerary embryonic stem cell lines may be used, if desired.

Adult stem cells can be isolated from mammalian tissue, including from any adult organ, umbilical cord blood, or placenta. The adult stem cells are multipotent, but they may be manipulated to provide pluripotent stem cells (iPSC) using conventional techniques.

ESC have great versatility but, compared to ASC, can be problematic for in vivo treatments due to the tendency of ESC to form teratoma. In contrast, ASC normally do not form teratoma and follow traditional lineage-specific differentiation patterns, fulfilling their physiologic homologous function of replacing normal turnover, aging or damaged tissues.

In one aspect, the stem cells can be derived from mammals, such as but not limited to rodents, pigs, cats, dogs, and primates, including humans.

Nonviable Pluripotent Stem Cells

As noted above, the pluripotent stem cells useful herein are nonviable. Advantageously, nonviable stem cells do not form teratomas. Surprisingly, nonviable pluripotent stem cells, including pluripotent stem cells that have been lethally irradiated or lyophilized into a powder, remain capable of improving age-related declines in tissue and organ function, as well as repairing damaged organs or tissues in a subject. No adverse effects have been noted after treatment. At least in some approaches, it has been found that lyophilized pluripotent stem cells have better efficacy than lethally irradiated pluripotent stem cells.

Prior to being rendered nonviable, the stem cells may be grown under suitable culture conditions. By one approach, the stem cells can be plated with a feeder layer for long-term culture of the stem cells. The feeder cells are treated so that the feeder cells do not divide during culturing. Human cells can be used as a feeder layer. For example, human fibroblasts, such as foreskin fibroblasts, can be used as a feeder layer. In one aspect, the stem cells are grown to about 70 percent confluence. In another aspect, the stem cells are grown on coated plates, such as plates coated with gelatin, laminin, collagen, recombinant human proteins, such as recombinant laminin or collagen, as well as commercially available substrates, such as MATRIGEL™ Basement Membrane Matrix from BD Biosciences, or combinations thereof, without a feeder layer for the final passages before collection for use in the methods described herein.

In one aspect, the stem cells may be made nonviable with irradiation, phototherapy, chemical treatment, and/or lyophilization. At least in some approaches, the method used should be effective to retain the intracellular contents of the stem cells. In one approach, the nonviable pluripotent stem cells useful herein also include nonviable fragments of pluripotent stem cells including vesicles or liposomal membrane encapsulated lyophilized pluripotent stem cell or fragments of pluripotent stem cells. These nonviable fragments may be used alone or in addition to non-viable but intact (i.e., cellular contents remain within the cell membrane) pluripotent stem cells. In another approach, the nonviable pluripotent stem cells useful herein are in the form of intact cells.

While there are a variety of techniques suitable for producing nonviable pluripotent stem cells, the following exemplary techniques are described in more detail. Other techniques may be used, if desired.

Lyophilization. In one approach, the pluripotent stem cells may be made nonviable by lyophilization. Generally, during lyophilization, water is removed from the cells after the cells are frozen and placed under vacuum so that ice in the product changes directly from solid to vapor without passing through the liquid phase. Other methods of freeze-drying or cryodesiccation may also be used, if desired, if the method selected does not have an adverse effect on the efficacy of the stem cells. Importantly, the lyophilized pluripotent stem cells in powdered form are not viable upon hydration, reconstitution, or suspension in liquid or other media, such as saline, before administration to a subject. The powdered cells can also be administered to a subject in powder form without reconstitution.

Lyophilization techniques may be used to provide a powdered pluripotent stem cell composition that is suitable for prolonged storage at room temperature or colder temperatures in sealed vials or ampules, for long periods of time. Lyophilization also allows for pre-production, ease of storage and transportation, and rapid availability for product delivery and access at the time of required treatment. Due to their indefinite shelf stability and ease of use, the lyophilized stem cells provide great flexibility to the applications in which the lyophilized pluripotent stem cell powder can be used.

By one approach, the pluripotent stem cells are prepared and cultured as described above and washed, such as with PBS, before collection and lyophilization. In this respect, the lyophilized cells do not include the media in which the cells were cultured (i.e., do not include conditioned media), thereby eliminating the possibility that the therapeutic benefit provided by the lyophilized stem cells can be attributed to conditioned media and any secreted factors, metabolites, proteins, or other components in the media.

An exemplary lyophilization technique that may be used is as follows. The cells are pretreated by dispersing them in a freezing solution and then freezing in liquid nitrogen. In one aspect, trehalose may be used as a lyoprotectant or freezing solution during the freezing step, but other lyoprotectants may also be used, if desired. The cells are then transferred to a lyophilizer that maintains a temperature low enough to keep the cells frozen. Vacuum is applied to lower atmospheric pressure to allow sublimation of water (i.e., transition of water from solid phase to vapor phase without forming an intermittent liquid). A variety of lyophilizers are commercially available, from bench top manifolds to very expensive large-scale production freeze driers. Lyophilization is advantageous in that it provides a storage-ready and stable product of stem cell contents in powder form with no viable residual cells or microbes.

At least in some approaches, lyophilization of the pluripotent stem cells preserves intact cell membranes. By one approach, the lyophilization conditions may be selected to substantially maintain the integrity of at least the cellular proteins so as to preserve protein structure and function but without any viable cells.

It was unexpectedly found that lyophilized pluripotent stem cells that are dead and desiccated were be at least as effective as, and in some instances surprisingly more effective than, lethally irradiated pluripotent stem cells that are able to live for hours or at most days in the body after administration to a subject. Many drugs and proteins cannot be lyophilized and then reconstituted to provide a composition having an efficacy similar to that of the drug or protein prior to lyophilization. Further, the ability of a cell to retain desired function after irradiation does not necessarily suggest its ability to retain desired function after lyophilization. Accordingly, it was unexpected that pluripotent stem cells could be lyophilized to provide non-viable cells (i.e., cells that are dead and desiccated) yet still provide a composition that is effective to improve age-related declines in tissue and organ function, as well as repairing damaged organs or tissues in a subject.

Radiation. In one aspect, the stem cells can be exposed to lethal doses of radiation, e.g., 100 Gy single fraction. The precise radiation dose delivered to the cells and length of dose is not critical so long as the cells are rendered nonviable. Other types of radiation, such as ultraviolet light, may also be used.

Inducing Growth Arrest or Apoptosis. In yet another aspect, the stem cells can be treated with an agent that induces growth arrest and/or apoptosis, such as but not limited to Mitomycin C, Actinomycin D, Camptothecin, Cycloheximide, Dexamethasone, Doxorubicin, Etoposide, and combinations thereof. Any other agent may be used that inhibits cell proliferation including but not limited to inhibitors of cellular components necessary for mitosis such as but not limited to protein synthesis, microtubule function, spindle check point unit, cell cycle specific kinases, cyclins, and or apoptotic inducing agents, as well as any means of genetic, protein, and or cell manipulation that will allow termination or prevention of unregulated or unlimited cell proliferation.

Treatment

In one approach, the methods described herein can be practiced within a short period of time after lyophilization or other form of lethal inactivation of the pluripotent stem cells. The methods described herein may also be practiced with stem cells that were previously lyophilized or lethally inactivated and packaged for storage. In one aspect, the formulation may be a powder or lyophilisate that is reconstituted in a liquid or other media of choice prior to use. In another aspect, liquid formulations can be prepared, such as, for example, in the form of a solution or suspension in a non-toxic, parenterally-acceptable solvent or diluent. In yet another aspect, the formulation may be in the form of an emulsion or liquid concentrate for dilution prior to administration. Exemplary pharmaceutically-acceptable carriers include saline, phosphate buffered saline, isotonic saline, Ringer's solution, dextrose, sterile water, deionized water, glycerol, ethanol, 5% dextrose in water, and combinations thereof. For topical application, the media to which the nonviable stem cells are added may include, for example, pharmaceutically acceptable carriers, such as creams, ointments, emulsions, and aqueous solutions.

In another approach, lyophilized pluripotent stem cell powder may be dispersed or rehydrated in a liquid media and added to a syringe, implantation device, or the like, depending upon the intended mode of delivery and use. In certain aspects, the lyophilized pluripotent stem cells may be provided in unit dosage form, such that an amount of the composition is provided in single or multi-dose dose containers.

The lyophilized pluripotent stem cell powder described herein may be administered to a subject by a variety of modes of administration, such as, for example, topical, enteral, or parenteral, and specifically including subcutaneous, intraperitoneal, intravascular, intramuscular, intramyocardial, intranasal, intrathecal, aerosolized, or transdermal. As such, the formulation as well as the concentration of the composition may vary. In one aspect, the compositions may be applied directly or topically to target tissues or organs, or to surrounding fluid or tissue. In one aspect, administration to the desired location may be done by catheter, infusion pump, or stent. Additional routes of delivery include topical application for treatment of the skin or wound.

The following examples are provided to illustrate certain aspects of the disclosure but should not be construed as limiting the scope of the disclosure. All publications and patents referenced herein are incorporated herein by reference in their entirety. Percentages and ratios are by weight unless specified otherwise.

EXAMPLES

Example 1—Preparation of Lyophilized Embryonic Stem Cells

Murine embryonic stem cells (ESC) were maintained feeder free with media containing 205 ml DMEM with glucose/sodium bicarbonate (Millipore, SLM-220-B), 37.5 ml ES Cell Qualified Feeder Bovine Serum (Millipore ES-009-C), 2.5 ml 100× Non-Essential Amino Acids (NEAA) (Millipore TMS-001-C), 2.5 ml L-glutamine solution (Millipore TMS-002-C), 2.5 ml 100× penicillin/streptomycin (Millipore TMS-AB2-C), and 12.5 µl Leukemia Inhibitor Factor (LIF) 10 UG (Millipore, LIF2010).

Figure 1:
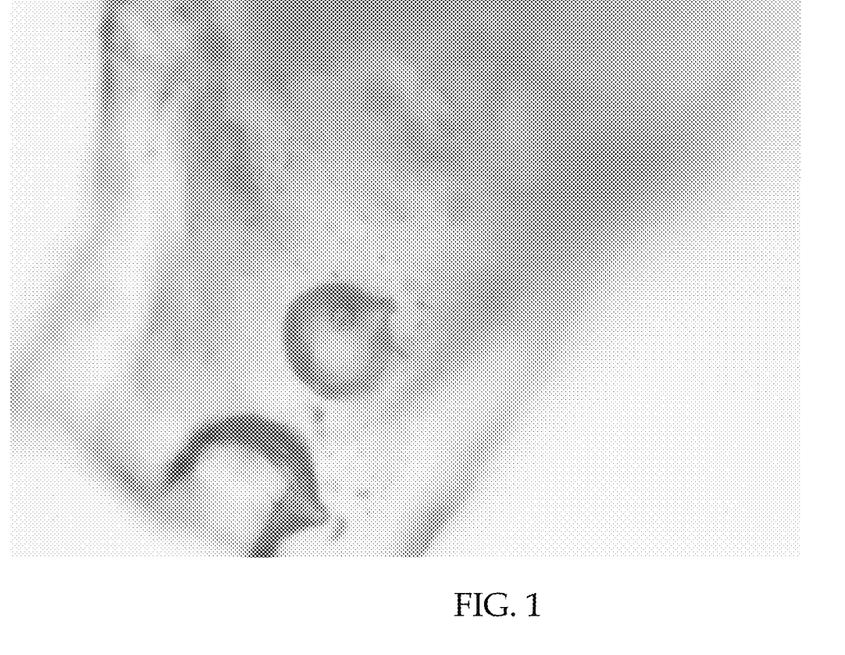
FIG. 1 is a microscopic picture of a lyophilized embryonic stem cell in trehelose matrix wherein the ESC is nonviable and fixed in a freeze-dried (lyophilized) state.

Approximately $1.0 \times 10^6$ ESC were suspended in 0.5 ml phosphate buffered saline with 0.1M trehalose (5) (Sigma Aldrich cat T0167) and 0.3 mg/dl EGCC (Zhejiant Yixin Pharmaceutical, Lanxi, Jinhua, Zhejiang, China) and cryopreserved at −80° C. Lyophilization was done at −80° C. and <0.008 torr using a Labconco Freezone 2.5 liter freeze dry system (Labconco Corporation, Kansas City, Mo.). Lyophilized ESC were stored at room temperature in a trehalose sugar matrix (FIG. 1).

Prior to use for injection, the sugar matrix dissolves when exposed to normal saline, leaving intact but non-viable ESC.

Example 2—Improvement of Age Related Learning and Memory Deficits in 18 Month Old Mice As a person ages, new learning becomes more difficult and long memory or retention of new events declines. The Morris water maze test quantifies both learning of new events and memory retention. On the first day ("training day"), a mouse is trained to find a raised platform in a tank of water. The maximum trial time is 60 seconds. If the mouse does not find the platform in 60 seconds, the mouse is placed on the platform. The first day tests how quickly the mouse learns to reach the escape platform. The mouse is tested on the second day ("test day") by being released in an opaque tank with the escape platform in the same location but now submerged. The second day is a test of long-term memory. The water tank is divided into four quadrants, and the escape platform always stays in the same location in the same quadrant. The mouse is placed in each quadrant next to the tank wall with its head facing the wall of the tank prior to release. The time to reach the escape platform is measured upon release of the mouse in each quadrant.

Eighteen month old B57B6 mice (Jackson Labs) mice (four in each group) received either 0.9% w/v NaCl saline, referred to herein as "normal saline" or "NS" (control), lyophilized ESC, or irradiated ESC. The lyophilized ESC and irradiated ESC were reconstituted in normal saline. The normal saline, lyophilized ESC (about $1-5 \times 10^6$ cells), or irradiated ESC (about $1-5 \times 10^6$ cells) were injected intraperitoneally (IP) once a week for three weeks.

Figure 2:
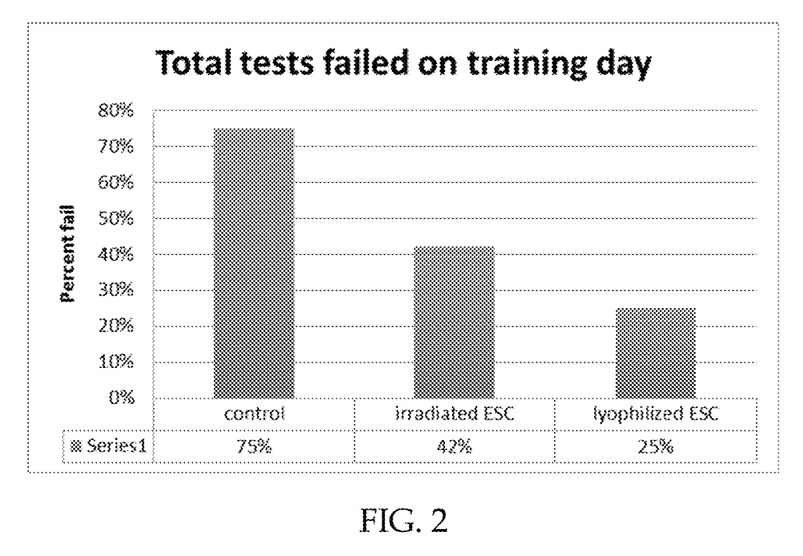
FIG. 2 is a bar graph showing the total percent of tests failed by aged (18 month old) mice on training day in a Morris Water Maze Test. Aged mice were treated with intraperitoneal (IP) injection of normal saline (NS; control), IP injection of irradiated embryonic stem cells (ESC) in NS, or IP injection of lyophilized ESC in NS.

The mice underwent the Morris Water Maze test one week after the third injection. The mice who had received either irradiated or lyophilized ESC learned much more quickly ($P<0.05$) than mice who received only normal saline. A test is deemed "failed" upon failure to reach the platform in 60 seconds. As shown in FIG. 2, the mice treated with the normal saline control failed 75% of the tests on training day, whereas the mice treated with irradiated ESC or lyophilized ESCS failed only 42% or 25%, respectively, of the tests on training day.

Figure 3:
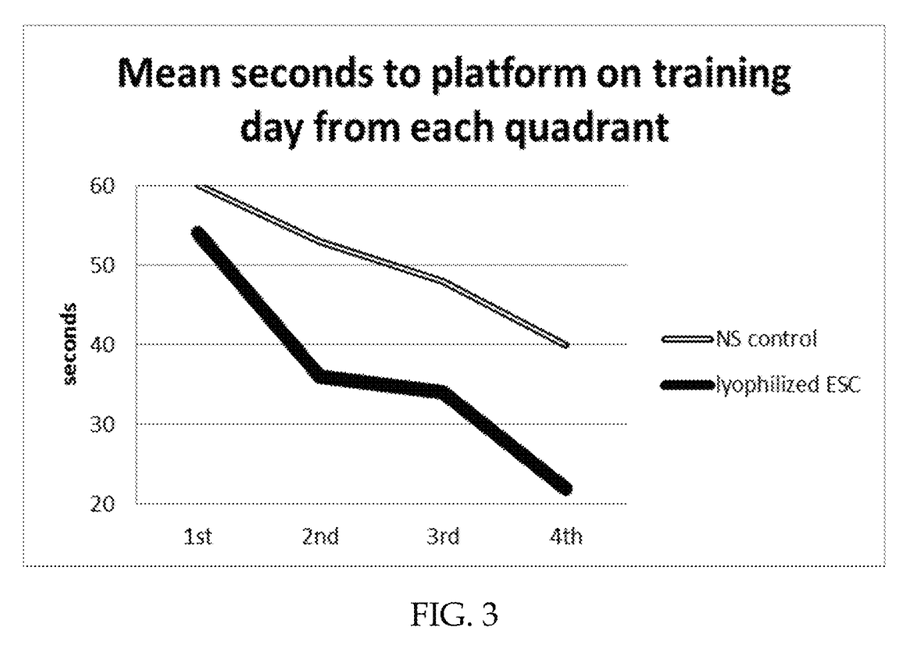
FIG. 3 is a line graph showing the training day improvement in time (in seconds) to the escape platform of aged (18 month old) mice in a Morris Water Maze test. Mice were treated with either intraperitoneal (IP) injection of normal saline (NS) or IP injection of lyophilized ESC dissolved in NS.

Although mice treated with irradiated ESC performed better than control mice, the mice treated with lyophilized ESC consistently performed better than mice receiving irradiated ESC. Therefore, further comparison was limited to only control mice and those treated with lyophilized ESC. As shown in FIG. 3, on training day, mice who received lyophilized ESC reached the escape platform faster ($P<0.05$) from each consecutive quadrant compared to control mice.

Figure 4:
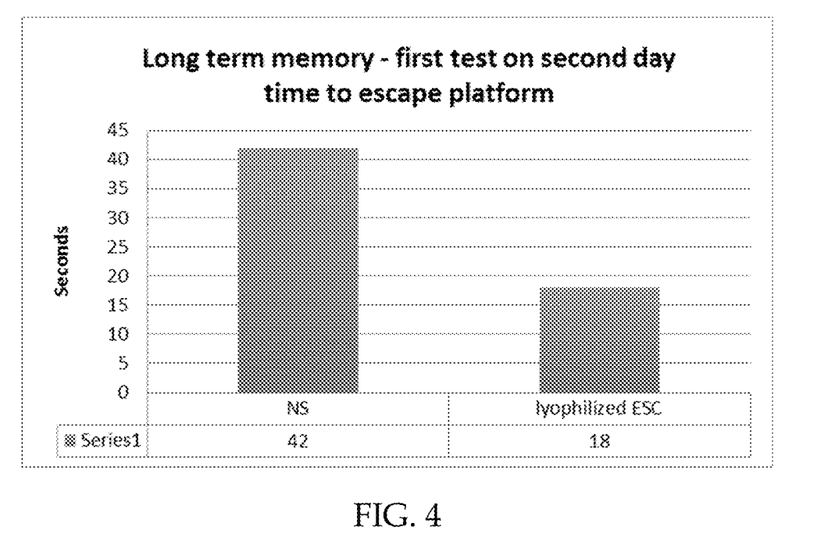
FIG. 4 is a bar graph showing the results of a long-term memory test of aged (18 month old) mice in the Morris Water Maze test. Mice were treated with either intraperitoneal (IP) injection of normal saline (NS) or IP injection of lyophilized ESC dissolved in NS.

Long-term memory is assessed by the amount of time taken to reach the escape platform on the first try of the second day (24 hours after training). As shown in FIG. 4, the mice treated with lyophilized ESC reached the escape platform more quickly than the control mice in the first attempt on the second day. Therefore, it was found that long-term memory was found to be significantly better in lyophilized ESC treated mice compared to control mice.

Figure 5:
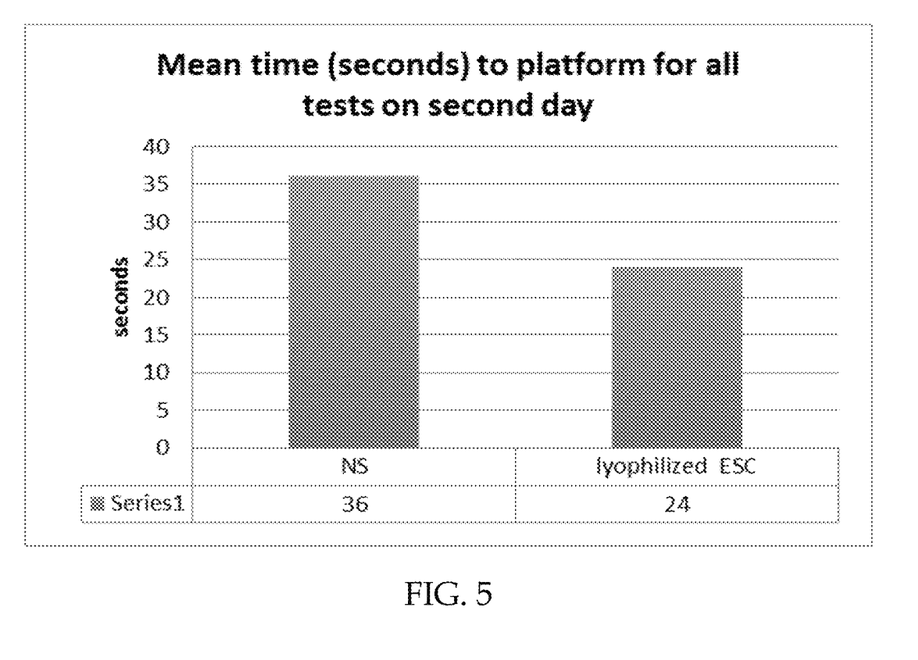
FIG. 5 is a bar graph showing the mean time to the escape platform of aged (18 month old) on the second day in the Morris Water Maze test. Mice were treated with either intraperitoneal (IP) injection of normal saline (NS) or IP injection of lyophilized ESC dissolved in NS.

As shown in FIG. 5, the mean time to the escape platform for all attempts from all four quadrants was also significantly better ($P<0.5$) in mice treated with lyophilized ESC.

Example 3—Improvement of Age Related Cardiac Dysfunction in 18 Month Old Mice

As a person ages, it has been found that the heart generally increases in weight, becomes stiffer, and has reduced contractility (i.e., a reduction in the maximum change in pressure with respect to time (dp/dt) during systole) and reduced diastolic relaxation (i.e., a reduction in the maximum change in pressure with respect to time (dp/dt) during diastole).

Eighteen month old B57B6 mice were evaluated for age related cardiac dysfunction. Four mice in each group received either normal saline ("NS"; control), lyophilized ESC, or irradiated ESC. The lyophilized ESC and irradiated ESC were reconstituted in normal saline. The normal saline, lyophilized ESC dissolved in NS (about $1-5 \times 10^6$ cells), or irradiated ESC suspended in NS (about $1-5 \times 10^6$ cells) were injected intraperitoneally (IP) once a week for three weeks. A Millar catheter was placed in the left ventricle to measure dp/dt (contractility and relaxation) one week after the third injection.

Cardiac contractility and relaxation (dp/dt) was measured via a high-fidelity transducer-tipped pressure catheter (SPR 839; Millar Instruments, Houston, Tex.) introduced via the carotid artery and into the left ventricle. Signals were digitized by use of a data translation series analog digital converter and then stored and analyzed on a Millar PVAN data acquisition and analysis system. Values derived from pressure traces were averaged over no less than 20 beats. The average of three signals each over 20 beats was obtained for contractility (+dp/dt maximal rate of change in systolic pressure (mmHg)/time (sec)) and relaxation (−dp/dt maximal rate of change in diastolic pressure).

Figure 6:
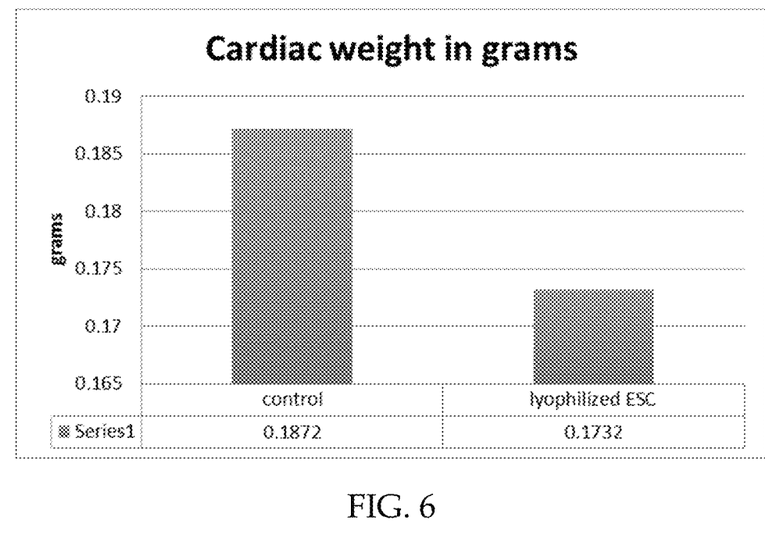
FIG. 6 is a bar graph showing cardiac weight in lyophilized ESC treated 18 month old mice versus saline treated control 18 month old mice.
Figure 7:
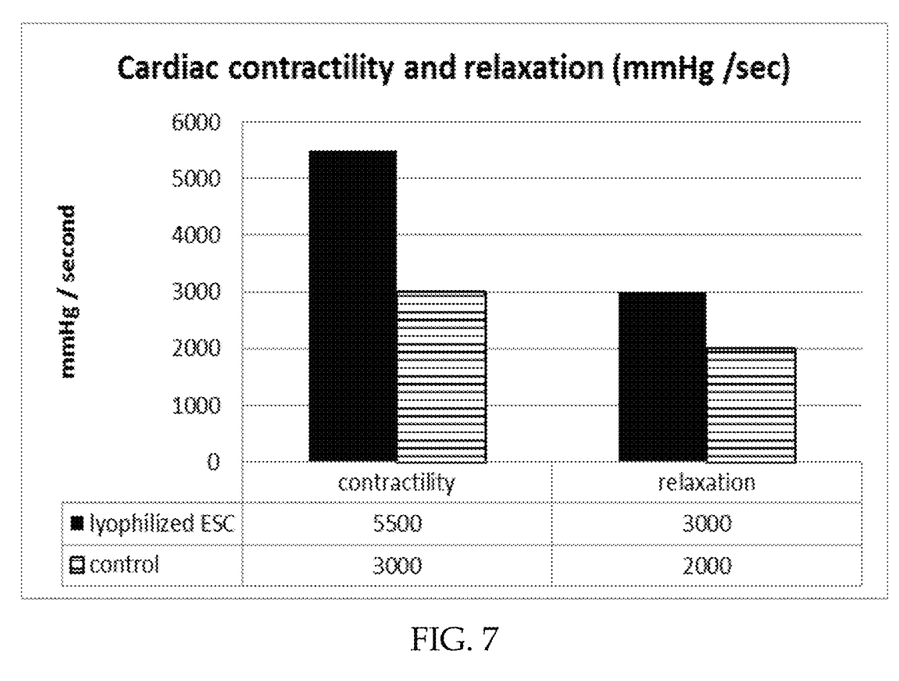
FIG. 7 is a bar graph showing cardiac contractility and relaxation after intraperitoneal treatment with lyophilized ESC versus intraperitoneal saline in eighteen month old mice.

Thereafter, the mice were euthanized, and the hearts were surgically removed and drained of blood and weighed. As shown in FIG. 6, the mice treated with lyophilized ESC had smaller lighter hearts (in grams) than the saline-treated control mice, which is consistent with a younger phenotype. As shown in FIG. 7, cardiac contractility was stronger and relaxation faster in lyophilized ESC treated mice, which is consistent with return of a more youthful heart function.

While the disclosure has been particularly described with reference to particular processes and embodiments, it will be appreciated that various alterations, modifications, and adaptations may be made by those skilled in the art based on the present disclosure and are intended to be within the spirit and scope of the embodied method as expressed in the appended claims.

REFERENCES

1. A Eggel et al., "A revival of parabiosis in biomedical research," Swiss Med Wkly, 2014 Feb. 4; 144:w13914.2.
2. M J Conboy et al., "Heterochronic parabiosis: historical perspective and methodical considerations for studies of aging and longevity," Aging Cell, 2013 June; 12(3): 525-30.

3. E. J. Eichwald et al., "The Anemia of Parabiotic Intoxication," Annals of The New York Academy of Sciences, vol 87, issue 1, December 2006
4. R K Burt et al., "Mitotically inactivated embryonic stem cells can be used as an in vivo feeder layer to nurse damaged myocardium after acute myocardial infarction: a preclinical study," Circ Res, 2012 Oct. 26; 111(10): 1286-96.
5. T. Higashiyama, "Novel functions and applications of trehalose," Pure Appl Chem 2002, vol 74, No 7, 1263-1269.
6. F S Loffredo et al., "Growth differentiation factor 11 is a circulating factor that reverses age-related cardiac hypertrophy," Cell. 2013 May 9; 153(4): 828-39.
7. I M Conboy et al., "Rejuvenation of aged progenitor cells by exposure to a young systemic environment," Nature. 2005 Feb. 17; 433(7027):760-4.
8. G S Baht et al., "Exposure to a youthful circulation rejuvenates bone repair through modulation of β-catenin," Nat Commun. 2015 May 19; 6:7131.
9. S A Villeda et al., "Young blood reverses age-related impairments in cognitive function and synaptic plasticity in mice," Nat Med. 2014 June; 20(6): 659-63.
10. G Song et al., "Use of the parabiotic model in studies of cutaneous wound healing to define the participation of circulating cells," Wound Repair Regen. 2010 July-August; 18(4):426-32.
11. J M Ruckh et al., "Rejuvenation of regeneration in the aging central nervous system," Cell Stem Cell. 2012 Jan. 6; 10(1):96-103.

What is claimed is:

1. A method of reducing cardiac size in a mammalian subject in need thereof, the method comprising intraperitoneally administering a stem cell composition consisting essentially of an amount of mammalian nonviable lyophilized pluripotent stem cells to a mammal in need thereof, wherein the mammalian nonviable lyophilized pluripotent stem cells are of the same species as the mammal in need thereof.
2. The method according to claim 1, further comprising preparing the composition by mixing the nonviable pluripotent stem cells with liquid media.
3. The method according to claim 2, wherein the liquid media comprises saline.
4. The method according to claim 1, wherein the subject is a human.
5. The method according to claim 1, wherein the stem cell composition does not include conditioned media.
6. The method according to claim 1, wherein the pluripotent stem cells are embryonic stem cells.

* * * * *